United States Patent [19]
Chingis et al.

[11] Patent Number: 6,049,027
[45] Date of Patent: Apr. 11, 2000

[54] HYBRID SORREL PLANT AND SEED

[76] Inventors: Murazgildin Chingis; Yalin Wang, both of Fu Hua Mansion D-12-E, No. 8 Chaoyangmen North Avenue, Dongcheng District, Beijing 100027, China

[21] Appl. No.: 08/965,784

[22] Filed: Nov. 7, 1997

Related U.S. Application Data

[60] Provisional application No. 60/030,630, Nov. 8, 1996.

[51] Int. Cl.⁷ .............................. A01H 5/12; A01H 5/00; A01H 1/04; A01H 5/10
[52] U.S. Cl. .......................... 800/298; 800/260; 47/58.1
[58] Field of Search .................................. 800/200, 260, 800/298; 47/58.1

[56] References Cited

PUBLICATIONS

K. Iwasaki, The Effectiveness of Salt–Accumulating Plants in Reclaiming Salinized Soils, Japan. J. Trop. Agr. 31 (4): 255–260, 1987.

P.D. Walton, Principles and Practices of Plant Science, Prentice Hall, Englewood Cliffs, N.J. p. 2–438 see for example, p397–413, 1988.

M. Islam–ul–Haq, et al., Reclamation of Saline and Alkaline Soils by Growing Kallar Grass, The Nucleus, 8,4, pp. 139–144, 1971.

E.W. Russell, The Role of Organic Matter in Soil Fertility, Phil. Trans. R. Soc. Lond, 281, 209–219, 1977.

*Primary Examiner*—David T. Fox
*Assistant Examiner*—Anne Marie Grünberg
*Attorney, Agent, or Firm*—Knobbe, Martens, Olson & Bear, LLP

[57] ABSTRACT

According to the invention, there is provided a hybrid forage spinach plant designated Modern Slam, which has the advantages of being drought-resistant, cold-resistant, flood-resistant, the ability to be grown in alkaline soils, and results in a high quality, high yield plant.

4 Claims, No Drawings

HYBRID SORREL PLANT AND SEED

This application claims benefit of provisional application No. 60/030,630 filed Nov. 8, 1996.

BACKGROUND OF THE INVENTION

This invention is in the field of sorrel breeding, relating specifically to a hybrid forage sorrel plant designated Modern SLAM.

At present, there are hundreds of billions square kilometers of dry, desert soils on the earth. China alone, for example, has 960 billion square kilometer waste land, of which 34.6 percent, or 332.7 billion square kilometer are comprised of desert soil. Because no effective development and utilization of these dry, sandy desert soils can be obtained, the condition of these soils grows worse and worse. Fertile soils and good farmland are being swallowed by these sandy, salty soils with astonishing speed. Since 1949, an area of land equal to twice the size of the Taiwan Province has been reduced to dry, desert-like land. China is currently supporting 22% of the world's population with only 7% of the world's cultivatable land.

Currently, no economically feasible way exists to improve sandy, salty alkaline soils. Traditional methods are tedious, expensive and not very effective. In order to meet the ever-increasing demand for food for both humans and animals, there is a need for a method of developing and reforming the desert soils of the world, making them suitable for agricultural purposes.

SUMMARY OF THE INVENTION

According to the invention, there is provided a hybrid sorrel plant, designated as Modern SLAM, produced by crossing English and Chinese varieties of sorrel. This invention thus relates to the hybrid Modern SLAM seed, the hybrid plant produced from the seed, and variants, mutants, and trivial modifications of Modern SLAM. This hybrid plant is characterized by superior yield, excellent vigor, and high protein, vitamin and mineral content. It is adapted for use in sandy, salty or clay-like soils, but performs best in dry, alkaline soils.

DETAILED DESCRIPTION OF THE PREFERRED EMBODIMENT

The present invention relates to a new species of sorrel which adapts to a salinized and dry environment. This new species has been designated "Modern SLAM." This new technology allows for the large scale improvement of salinized and sandy soils, turning waste into wealth, and has significant advantages over current methods for the improvement and control of saline-alkali soils.

This invention includes hybrid seed of Modern SLAM and the hybrid plant produced therefrom. As used herein, the term plant includes plant cells, plant protoplasts, plant cell tissue cultures from which plants can be regenerated, plant calli, plant clumps, and plant cells that are intact in plants, or parts of plants.

Modern SLAM is a type of high-stalk sorrel, created by the hybridization of Chinese and English sorrel varieties. It is adapted for growth in alkaine soils, is drought-resistant, cold-resistant, fast growing, and produces a high quality yield. It is a perennial plant which can grow for as long as 25 years, with yields of more than 200 tons/hectare. This new species contains high levels of protein, Vitamin C, selenium and other nutrients.

The plant remains dormant during the winter, with any residual vegetation falling to the earth. The plant grows again in the spring, and can be harvested in the late spring and early fall. In the third year of life, Modern SLAM will grow as high as 2.5–3 meters, and can be harvested 3–4 times throughout the growing season. The roots grow 1.5–2 meters deep to support the rapid growth of the plant. The plant can be grown for as long as 25 years, with maximum yield achieved in the fifteenth year. Production slowly declines after that time.

Modern SLAM can be grown in basic soil (pH 8.0–12.0). It acts to break up the soil without the need to add gypsum. It reduces the salinity of the soil. Modern SLAM thrives in hot, windy desert climates, as well as cold dry climates. Production reaches between 200–400 tons/hectare. Seeds of the Modern SLAM plant were deposited with the American Type Culture Collection (ATCC), 10801 University Boulevard, Manassas, Va. 20110-2209, on Mar. 8, 1999, and assigned ATCC Accession No. 203827.

Preparation of Seeds for Planting The fruit of the SLAM plant is a kind of three arris nut The inner cuticle contains a glue-like substance. Preferably, this substance is removed from the seeds prior to planting by treatment with 1(XATP). This treatment promotes germination of the seed.

Once the seeds are obtained and prior to planting the SLAM seeds, it is preferred that they be placed in warm water (approximately 52° C.) for about 20 minutes. The seeds are removed and rinsed in cold water, then placed in a strainer out of direct sunlight to dry. Alternatively, a $CuSO_4$ wash can be used to treat the seeds before planting.

Preparation of the Soil for Planting

Modern SLAM is suitable for planting in saline soil, wet meadow alkali soil, saline wet meadow soil, saline wet meadow desert soil, and alkaline soil. The soil is turned using 3–5% SCHO, a soil opsonic agent, which is mixed well into the soil. The soil is then soaked with water. The seeds are placed at a depth of 2–2.5 cm and covered with soil. Any clods in the soil should be reduced to fine particles during the preparation of the soil for planting.

Growth of the Plant

If within the first 5–7 days of planting the seeds no rain has fallen, the ground should be watered. If the temperature is too high, the seeded area should be covered with cut vegetation or other cover to protect the seedlings. Within 3–4 days after planting, the first sprouts should appear. The rate of sprouting is approximately 97%. The length of the root is longer than that of the leaf in the young plant. When the plant has developed 4–5 leaves, the ratio of leaf length to root length is almost 1:3. The speed of the root growth allows the plant to survive in hot, dry climates.

Like many perennials, SLAM does not form a main branch in the first year, only growing roots and lush leaves. To protect the plant during its first winter, the plant is sprayed with the biochemical reagent 2(CHON) to promote growth of the roots and to assure growth of a seedling in the second year.

Starting in the second year, the growth period lasts for approximately 60 days. During the growing peak, SLAM grows 7–8 cm per day. After about 3 months, the plant will produce 60–80 leaves up to about 100 cm high, with each leaf weighing approximately 2.5 kg. The root of the SLAM plant reaches 40–50 cm in length, with a thickness of approximately 2–3 cm.

Harvesting and Processing

The plant is harvested three times during the growing season, late May, late July, and late September. Modern SLAM can be used as human food, livestock feed, and as raw material for the production of plant protein and various extracts. The plant can be processed to remove the protein, fat, vitamins and other nutrients. The vegetable protein content in the stem and leaves of SLAM is similar to that of soybean. SLAM is also rich in Vitamin C, Vitamin A, glutamic acid, lysine, methionine and iron. The protein can be extracted, and the remaining material processed to remove vitamins, minerals and unsaturated fatty acids. The components of a 2.5 kg SLAM sample grown for 40 days is shown below in Table 1.

TABLE 1

Components of SLAM

| | | | |
|---|---|---|---|
| Crude Protein: | 27.07% | Vc: | 580 mg/kg |
| Crude Fiber: | 10.44% | V4: | 800 mg/kg |
| Crude Fat: | 5.24% | Ve: | 20.23 mg/kg |
| Crude Ash: | 18.94% | Aneurine: | 1.94 mg/kg |
| Calcium | 2.81% | Ovoflavin: | 5.97 mg/kg |
| Phosphorus: | 0.50% | Niacin: | 273.29 mg/kg |
| Dry Matter: | 9.66% | Pteroglutamic: | 6.64 mg/kg |
| Nitrogen-free Extract: | 3.93% | Choline: | 120 mg/kg |
| | | Iron: | 2032 mg/kg |
| Copper: | 27.29 mg/kg | Selenium: | 1.02 mg/kg |
| Zinc: | 48.11 mg/kg | Manganese: | 73.65 mg/kg |
| Aspartic acid: | 1.147% | Leucine: | 0.987% |
| Threonine: | 0.625% | Tyrosine: | 0.475% |
| Serine: | 0.619% | Phenylalanine: | 0.712% |
| Glutamic acid: | 3.837% | Lysine: | 0.600% |
| Proline: | 0.864% | Methionine: | 0.406% |
| Glycine: | 0.722% | Histidine: | 0.406% |
| Alanine: | 0.784% | Arginine: | 0.578% |
| Cystine: | 0.120% | Meth/Aneurin: | 0.191% |
| Valine: | 0.889% | Isoleucine: | 0.441% |

A further analysis was performed to determine the content of 1000 g of SLAM dry matter during the various stages of plant growth. The results of this analysis is shown below in Table 2.

TABLE 2

Content of 1000 g SLAM During Various Growth Periods

| | leaf fascicle | producing shoots | floral initiation | early flowering | flowering in harvesting |
|---|---|---|---|---|---|
| dry matter in grams | 86.8 | 107.9 | 109.7 | 119.0 | 127.8 |
| protein % | 38.94 | 39.81 | 29.94 | 27.81 | 20.56 |
| nitrogen-free | 33.67 | 30.74 | 34.50 | 42.98 | 38.93 |

TABLE 2-continued

Content of 1000 g SLAM During Various Growth Periods

| | leaf fascicle | producing shoots | floral initiation | early flowering | flowering in harvesting |
|---|---|---|---|---|---|
| extract % sugar % | 13.54 | 9.87 | 15.39 | 5.23 | 5.71 |
| fat % | 6.07 | 5.04 | 4.54 | 3.17 | 2.27 |
| ashy substance % | 11.88 | 10.53 | 9.13 | 8.52 | 7.65 |
| vitamin C mg | 792.05 | 760.41 | 311.86 | 149.17 | 160.72 |
| carotene mg | 55.48 | 57.69 | 58.61 | 31.28 | 20.34 |

Thus, the present invention provides a hybrid sorrel plant, characterized by superior yield and high protein, vitamin and mineral content. It is adapted for use in dry, salty, alkaline soils, and can be used to improve these types of soil.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A sorrel plant or its parts, produced by seed designated Modern SLAM, representative seed having been deposited under ATCC Accession No. 203827.

2. Sorrel seed designated Modern SLAM, representative seed having been deposited under ATCC Accession No. 203827.

3. A method of reducing the salinity of soil comprising planting sorrel seed designated Modern SLAM, representative seed having been deposited under ATCC Accession No. 203827, in said soil.

4. A method of breaking up soil having a high clay content comprising planting sorrel seed designated Modern SLAM, representative seed having been deposited under ATCC Accession No. 203827, in said soil.

* * * * *